United States Patent [19]

Murphy

[11] Patent Number: 4,685,906
[45] Date of Patent: Aug. 11, 1987

[54] EYE-DROPS APPLICATION DEVICE

[76] Inventor: William F. Murphy, 5 Denson Dr., Edgewater, Fla. 32032

[21] Appl. No.: 845,948

[22] Filed: Mar. 31, 1986

[51] Int. Cl.⁴ ............................................. A61M 35/00
[52] U.S. Cl. ..................................... 604/300; 604/301
[58] Field of Search ............. 16/114 R; 222/192, 212, 222/215, 420; 604/290, 293-295, 297, 300-302

[56] References Cited

U.S. PATENT DOCUMENTS 4,200,323 4/1980 Cocksedge ...................... 16/114 R
4,296,958 10/1981 Stranders ......................... 16/114 R
4,531,944 7/1985 Bechtle .............................. 604/30 Z

FOREIGN PATENT DOCUMENTS 682345 5/1930 France ................................. 604/297
2142829 1/1985 United Kingdom ................ 604/295

Primary Examiner—C. Fred Rosenbaum
Assistant Examiner—J. L. Kruter
Attorney, Agent, or Firm—Murray and Whisenhunt

[57] ABSTRACT

Device for administering eye drops from an eye dropper bottle comprising a frame having a first ring member configured to fit around an eye of a person, and a second ring member for supporting the eye dropper bottle while drops are dispensed from the bottle into the eye. The frame includes at least two discrete connecting rods connected to the first and second ring members for maintaining the ring members in a fixed spaced-apart configuration with respect to each other. To reduce the risk of contaminating the drops, the device is configured so that there is no surface of the device which is contactable by drops entering the eye. A handle may be connected to the second ring member for facilitating handling of the device.

12 Claims, 7 Drawing Figures

EYE-DROPS APPLICATION DEVICE

The present invention relates to an improved device for use in administering eye drops from an eye dropper dispenser into the eye of a user.

BACKGROUND OF THE INVENTION

The use of eye dropper bottles, for example soft-sided squeeze bottles, having a nozzle with a discharge opening for applying drops of medication or cleansing fluids directly into the eye is conventional and well-known. It is also well known that considerable difficulty is often encountered in trying to hold the hand steady enough to ensure that the liquid from the eye dropper bottle drops into the correct place in the eye and, with squeeze bottles, the bottle often moves sufficiently when squeezed to cause the liquid to miss the eye and fall onto the face, which is both irritating and wasteful. A further problem which is often encountered with the use of eye dropper bottles is that when the user is looking directly upward at the end of the dropper, the distance of the lower end of the dropper from the eye cannot be accurately determined, and this gives rise to the danger of the eyeball being contacted by the dropper, thereby increasing the risk of damage and infection to the eye. The above problems are especially acute with users who are elderly, nervous, suffer from hand tremors, or who generally lack adequate coordination.

As a result of the above difficulties, considerable efforts have been made in the past to develop devices which facilitate the administration of eye drops. Numerous patents have issued relating to various forms of such devices, and some of these are discussed below.

U.S. Pat. No. 2,482,431 discloses a combination eye dropper and eye cup. The cup portion fits comfortably over the eye socket of the user and maintains a reservoir of eye wash solution in contact with the eyeball during the washing operation. The device includes an eye dropper, and when it is desired to administer drops into the eye, the eye dropper is removed from the cup and used separately.

U.S. Pat. No. 2,676,592 relates to an eye dropper having a portion which rests upon the bridge of the user's nose. A portion extends over the eye to be treated carrying a means for supporting an eye dropper above the eye.

U.S. Pat. No. 2,898,911 relates to a device for dispensing drops of medicament into the corner of the eye rather than onto the center of the eyeball. The device comprises a cup which is eccentrically disposed relative to the nozzle of the eye dropper.

U.S. Pat. No. 3,016,898 relates to a eye fluid applicator having an auxiliary chamber mounted on top of an eye cup. A valve arrangementg may be provided in the auxiliary chamber in order to ensure administration of precise quantities of fluid to the eye.

U.S. Pat. No. 3,058,466 discloses various bridge devices for self-administration of medication to the eye. These devices are designed to bridge the forehead and the cheek of the user, and an opening may be provided in the bridge to permit the user's finger to engage the eyelid and extend it to provide a trap for the medication.

U.S. Pat. No. 3,872,865 relates to an eye drop dispenser which is provided with a "bumper" around the nozzle in order to protect the eye from contact with the nozzle. The bumper is a separate component which fits around the body of the container, generally by a press fit.

U.S. Pat. No. 3,934,590 discloses a droplet dispensing device having a tripod configuration, in which one of the legs of the tripod is notched for mounting on the bridge of the nose of the user. The other two legs rest on the user's cheekbone and brow respectively, and the eye dropper dispenser is housed in a container from which the three legs of the tripod extend.

U.S. Pat. No. 4,085,750 describes various eye drop bottle attachments for facilitating the administration ofeyedrops into the eye of a user. The attachments are characterized by a pair of flexible arms having pads on their ends. In use, the arms are squeezed together and pressed gently against the closed eyelids so that when released, the eyelids are forced apart as the arms flex back to their unflexed position. In this way, the eye is held open while the drops are administered.

OBJECTS OF THE INVENTION

A disadvantage associated with many, if not all, of the prior devices is that, unless the head is completely held back so that the face is essentially horizontal, eye dropper fluid most likely will contact a surface of the device during administration, thereby increasing the chances of contamination of the fluid and resulting eye infection. In an effort to overcome this contamination problem, it is a principal object of the present invention to provide a device for use in administering eye drops to an eye which is configured so that even if the head is not held completely back no surface of the device is contactable by eyedropper fluid entering the eye.

It is another object of the present invention to provide a device for use in administering eyedrops to an eye, which is lightweight, easy to use, does not reduce the amount of light entering the eye during use of the device, and eliminates contact between the eyedropper and the eye thereby reducing the risk of damage and/or infection to the eye.

It is another object of the present invention to provide a device for use in administering eyedrops to an eye which does not require the user to bend the head back so that the face is approximately horizontal.

It is another object of the present invention to provide a device for use in administering eyedrops to an eye wwhich can be readily used by a right or left-handed person.

It is another object of the present invention to provide a device for use in administering eyedrops to an eye which can be fabricated on a low-cost basis, is easy to clean, and is made of a heat-resistant material which can be conveniently sterilized.

It is a yet further object of the present invention to provide a device for use in administering eyedrops to an eye in which at least a part of the device is made of a material, such as, for example, a flexible plastic material which allows the device to be readily conformed to the shape of the eye region of the user, especially the orbital rim shape.

SUMMARY OF THE INVENTION

In accordance with the invention, there is provided, according to one embodiment, a device for use in administering eyedrops from an eyedropper dispenser into an eye, comprising a frame having a first ring member configured to fit around the eye of the user, and a second ring member for supporting the eyedropper dispenser above the eye while the drops are dispensed into the eye. At least two discrete connecting members are connected to the first and second ring members for maintaining the ring members in a spaced-apart configuration by a distance so as to avoid any possibility of contact between the eye of the user and the eyedropper dispenser. To reduce the risk of contamination, the device is configured so that there is no surface of the device which is contactable by eyedropper fluid entering the eye. A handle may be mounted to the frame, preferably removable mounted to the second ring member, in order to facilitate easy placement of the device in the region of the orbital rim of the user.

According to a preferred aspect, the first and second ring members are disposed at an angle to each other so that it is not necessary for the user to bend the head completely back while drops are being administered to the eye.

BRIEF DESCRIPTION OF THE DRAWINGS

Embodiments of the invention will now be described, with reference to the accompanying drawings, in which.

DETAILED DESCRIPTION OF THE INVENTION

Figure 1:
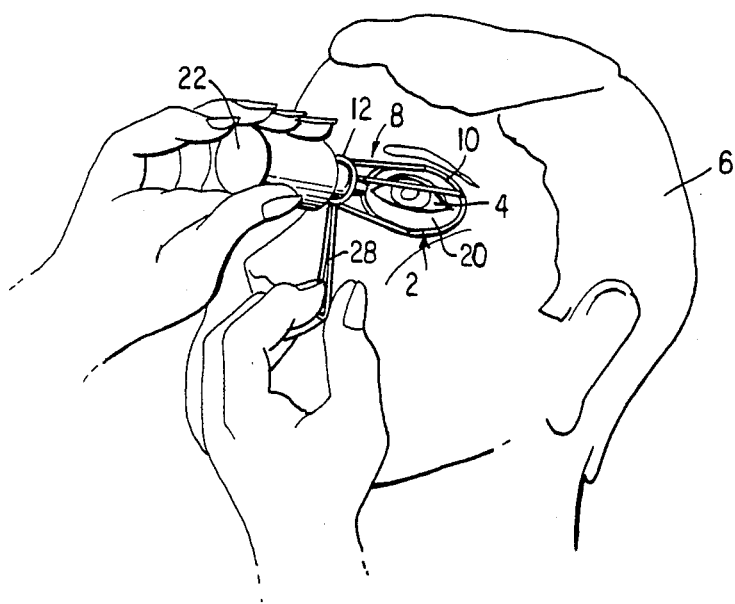
FIG. 1 is a perspective view showing the manner in which an embodiment of the device of the invention is used for administering drops to the eye of a user.
Figure 2:
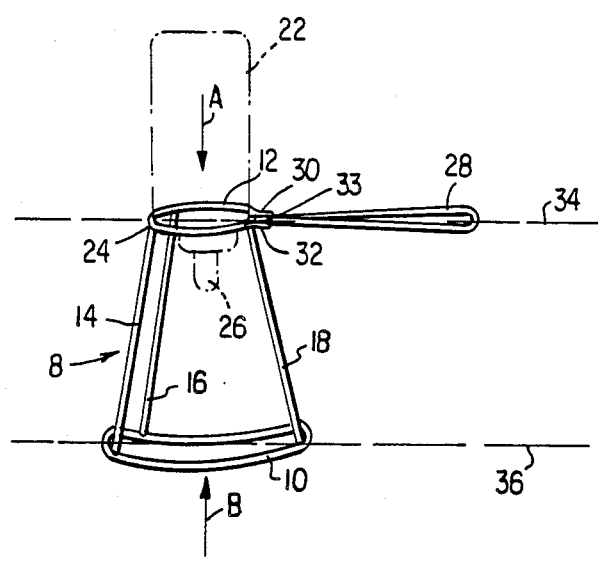
FIG. 2 is a side view of a device of the invention.

Referring to FIGS. 1 and 2, there is shown a device of the invention, generally referenced 2, in position about an eye 4 of user 6. The device includes a frame 8 having a first ring member 10 and a second ring member 12 connected together in spaced-apart relation by connecting members 14, 16, 18. The frame 8 may be fabricated from metal such as, for example, stainless steel or an alloy which possesses a good tensile strength and can be sterilized. Alternatively, the frame may be fabricated from a suitable rigid heat resistant plastic material such as, for example, polypropylene. It is desirable for at least the first ring member 10 to possess some flexibility so that it can be shaped by the user to comfortably fit about the orbital rim, generally referenced 20, of the user.

As shown in FIG. 2, the connecting members 14, 16, 18 are discrete rods which are fixedly mounted to the first and second ring members 10, 12. The number of connecting members is not critical, provided that the first and second ring members are maintained in the desired spaced-apart configuration. Thus, the device as illustrated in the drawings has three connecting members 14, 16, 18, but this number is not critical, and the device may include only two connecting members or may contain more than three, as desired. While not critical, it is preferred that the connecting members 14, 16, 18 are equi-circumferentially disposed around each of the first and second ring members 10, 12.

Figure 4:
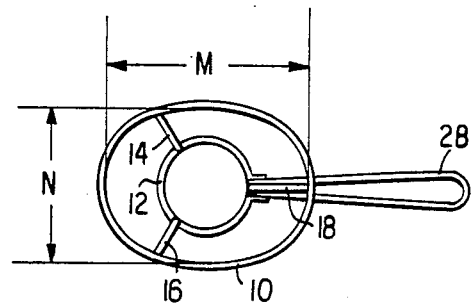
FIG. 4 is a plan view of the device shown in FIG. 2 in the direction of arrow B.
Figure 3:
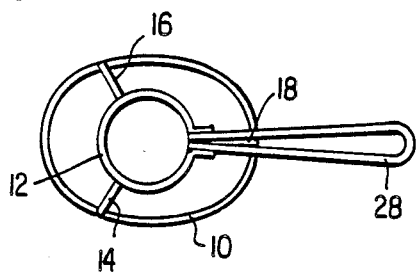
FIG. 3 is a plan view of the device shown in FIG. 2 in the direction of arrow A.

As can be seen from FIGS. 3 and 4, the first ring member has a shape approximating that of an ellipse, and the second ring member is approximately circular in shape. As can be seen from FIG. 2, the first ring member is generally non-planar, and has an elliptical configuration which conforms approximately to the orbital rim 20 of the eye of the user. While the invention is not limited to specific dimensions, the first ring member 10 generally has a major axis M of about 1½ inches, and a minor axis N of about 1 5/16 inch. The dimensions may vary, for example if the device is intended for use by children. The second ring member generally has a diameter of ¾ inch or less, for example 23/32 inch, and is designed to accommodate a commonly available eye dispenser dropper bottle 22 as shown in FIG. 1 and also in dotted outline in Figure 2. The bottle 22 has a shoulder portion 24, from which a nozzle 26 projects, and the diameter of the second ring member is designed so as to permit the nozzle 26 to project through the ring while supporting the shoulder portion 24 on the ring, as can be seen in FIG. 2. Contact between the nozzle 26 and the eye 4 is also prevented by ensuring that the connecting rods 14, 16, 18 are of sufficient length. In this regard, it is preferred that each connecting rod is of the order of 1¼ to 1¾ inches long, for example 1½ inches long.

The present device is configured so that no surface of the device is contactable by eyedropper fluid which enters the eye. This reduces the risk of eye infection arising due to the fluid becoming contaminated as a result of contacting a surface of the device prior to entering the eye. The only contact occurring between the fluid and the device will be with fluid flowing away from the eye and coming in contact with a lower portion of the first ring member 10 (see FIGS. 1 and 3). Any fluid which does enter the eye will not have contacted any surface of the device prior to entering the eye, thereby significantly reducing the risk of infection.

As can be seen from the drawings, the device of the invention may be provided with a handle 28, although this is not a critical requirement since the user can handle the device by gripping the connecting rods 14, 16, 18 at a location near the second ring member 12. However, it is preferred to provide a handle connected to the frame 8, and a handle may be conveniently attached to the second ring member 12 at a point 30 where the second ring member is also attached to one of the connecting rods 18. The handle 28 may be fabricated from the same material as the frame and preferably is removably mounted. This not only facilitates packaging and reduction in packaging costs, but also enables use under varying conditions. Removability of the handle 28 from the frame 8 may be achieved, for example, by providing a tubular portion 32 at the end of the handle which facilitates a push-fit to a rod 33 fixed to the second ring member 12 of the same diameter as the internal diameter of the tubular portion (see FIG. 2). While the handle may be of any convenient form, it is preferred that the handle is in the shape of an elongated loop, as can be clearly seen in FIG. 3. Any length of handle may be employed for example 1½ to 2 inches, typically 1⅞ inches. It is also preferred that the handle 28 extends generally in a plane 34 passing through the second ring member 12, as can be clearly seen from FIG. 2. In the embodiment illustrated in FIG. 2, a second plane 36 can be seen extending generally through the first ring member 10, and the planes 34, 36 are substantially parallel to each other.

When the device illustrated in FIGS. 1 through 4 is used, it is gripped by the handle 28 and positioned about the eye as shown in FIG. 1. Because of the generally non-planar configuration of the first ring member 10, it is possible to adjust the angle of inclination of the frame with respect to the eye so that drops can be administered from the dispenser bottle 22 without having to bend the head back so that the eye is disposed horizontally or approximately horizontally. The bottle 22 is then located in the second ring member 12, and the drops are administered in the usual way by squeezing the bottle gently. If drops are to be administered to both eyes, after application to the first eye has been completed, the device 2 is simply transferred to the second eye, and the dispensing operation is repeated, as described above.

Figure 5:
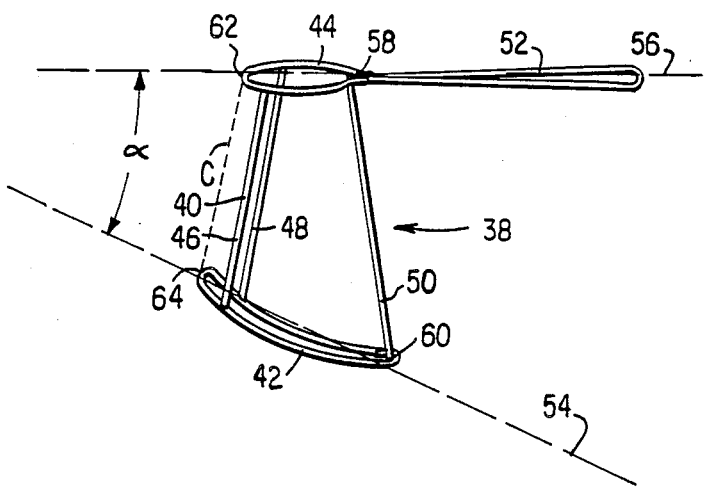
FIG. 5 is a side view of another embodiment of the device of the invention.
Figure 6:
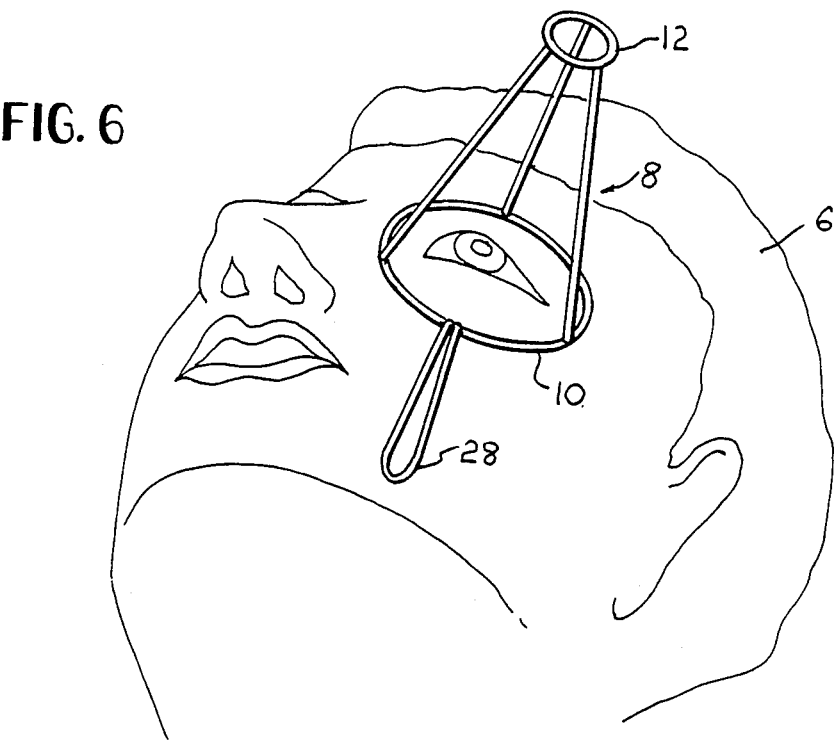
FIGS. 6 and 7 are further perspective views showing use of the device of the present invention.
Figure 7:
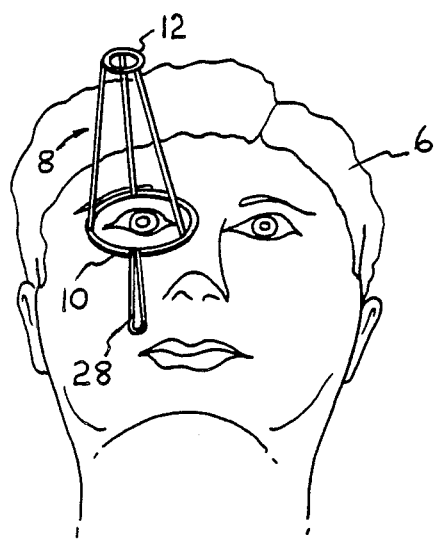

In order to reduce even further the extent to which the head of the user has to be tilted back prior to administering the drops, a second embodiment of the device of the invention has been developed, and this is illustrated in FIG. 5. The device, generally referenced 38, includes a frame 40 with first and second ring members 42, 44 and connecting members 46, 48, 50. The first ring member 42 is disposed in a plane 54 and the second ring member 44 is disposed in a plane 56. As can be seen from FIG. 5, the plane 54 is inclined at an angle α to the plane 56, with that angle being approximately 25 to 40 degrees, for example about 30 degrees. By arranging the first ring member at an angle to the second ring member, it is possible to position the device about the eye so that the device is inclined upwardly while the user's head is only slightly backwardly inclined. As can be seen from FIG. 5, the connecting member 50 is longer than the connecting members 46, 48 which are both generally of equal length. While the invention is not limited to specific dimensions, it is preferred that the connecting member 50 have a length of the order of 1¾ inches measured from point 58 where the connecting member 50 meets the second ring member 44 to the mid-point 60 in the bend of the first ring member 42. The distance C measured from point 62 on the second ring member 44 to the mid-point 64 in the bend on the opposite side of the first ring member from the midpoint 60 may be about 1¼ inches.

The device of FIG. 5 is used in the same way as described above for the device illustrated in FIGS. 1 through 4. As with the device of FIGS. 1 through 4, it is not critical for the device of FIG. 5 to have a handle 52, since the frame can be gripped by the user at the upper portion of the connecting members 46, 48, 50, near the second ring member 44. However, it is preferred for the handle 52 to be provided so that the device is handled by the user at a point remote from the area where the drops are dispensed in order to avoid the risk of the drops touching the fingers of the user and other possible sources of contamination. The handle 52 may also be removable in the same way as described above in connection with the embodiment illustrated in FIGS. 1 through 4.

From the above, it will be appreciated, that numerous advantages are enjoyed by the device of the invention. In particular, the chance of eye infection is significantly reduced as there is no surface of the frame which is contactable by fluid entering the eye. The device is simple and easy to use, and can be employed for administering drops to both eyes without the user having to transfer the device from one hand to the other when moving from one eye to the other. The frame structure of the device renders it lightweight and does not result in any reduction in the amount of light entering the eye, so that the vision of the user is not impaired during the use of the device. The open frame structure also facilitates easy cleaning of the device, as well as sterilization from time to time to remove contamination. The device can be produced in large numbers on a low-cost basis, and this makes the device very attractive from a commercial standpoint. The device can be used with any of the commercially available eyedrop dispensers, and the loose fit of the bottle in the second ring member enables the user to easily adjust the angle at which the drops are dispensed to ensure that the drops enter the eye at the correct place. Location of the device on the eye is also facilitated by the first ring member which is shaped to conform with the orbital rim of the user, and this further increases the ease of use of the device. The embodiment illustrated in FIG. 5 has the further advantage that the head of the user need not be tilted back very far in order to achieve the desired angle of administration of the drops into the eye. Finally, any contact of the eye with the eyedrop dispenser is avoided by ensuring that the connecting members joining the first and second ring members are of a length which is sufficient to ensure that the nozzle of the dispensing bottle is maintained completely out of contact with the surface of the eye.

I claim:

1. A device for administering eyedrops from an eyedropper dispenser, said device comprising a frame including:
    a first annular closed ring member means configured to fit around the orbit of an eye of a user for supporting and adjusting the angle of inclination of the frame in the socket of the eye to achieve a desired angle about the eye out of the vertical for dispensing eyedrops into the eye when the user's head is in a tilted-back position other than a prone position, said first ring member means being disposed in a first plane;
    a second annular closed ring member means for supporting an eyedropper dispenser while drops are dispensed into said eye, said second ring member means allowing variable angular adjustment of said dispenser when the user's head is in other than a horizontal back-prone position, said second ring member means being disposed in a second plane, said second plane being disposed at an acute angle with respect to said first plane, such that said first and second ring members are in a spaced-apart angularly inclined configuration with respect to each other;
    a rigid handle member means connected to and extending from said first ring member means, said handle member means extending in said first plane of said first ring member means, for allowing a user to adjust said first ring member means in the socket of the eye to achieve said desired angle about the eye; and
    at least two discrete rod connecting members connected to said first and second ring member means for maintaining said first and second ring member means in said spaced-apart angularly inclined configuration.

2. A device according to claim 1, wherein said first ring member means has a shape approximately that of an ellipse for fitting comfortably around the orbit of the eye of the user.

3. A device according to claim 2, wherein said ellipse has a major axis of about 1½ inches and a minor of about 1 5/16 inches.

4. A device according to claim 2, wherein said first ring member means has a generally non-planar elliptical configuration which conforms approximately to the orbit of the eye of the user.

5. A device according to claim 1, wherein said second ring member means has a shape approximately that of a circle.

6. A device according to claim 5, wherein said circle has a diameter of about $\frac{3}{4}$ of an inch.

7. A device according to claim 1, wherein said acute angle is of the order of 25° to 40°.

8. A device according to claim 7, wherein said acute angle is about 30°.

9. A device according to claim 1, wherein said device includes three discrete rod connecting members equicircumferentially spaced between said first and second ring member means.

10. A device according to claim 9, wherein two of said discrete rod connecting members are about $1\frac{1}{4}$ inches in length, and the third discrete rod connecting member is about $1\frac{3}{4}$ inches in length.

11. A device according to claim 1, which is fabricated from metal.

12. A device according to claim 1, which is fabricated from a heat-resistant plastic material.

* * * * *